July 20, 1976 W. A. WARRINER Plant Pat. 3,937
ROSE PLANT
Filed April 30, 1975
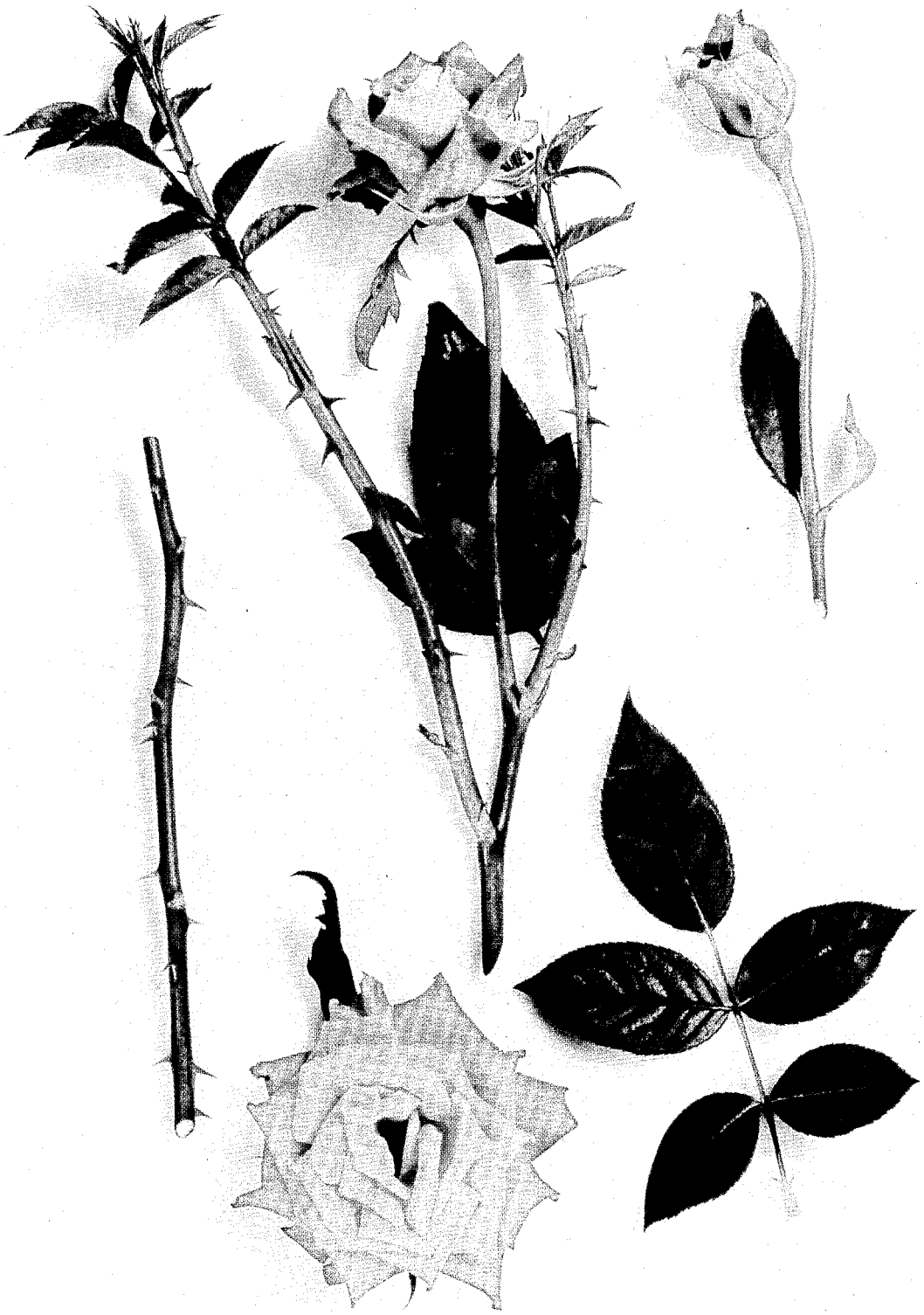

United States Patent

Plant Pat. 3,937

Patented July 20, 1976

3,937

ROSE PLANT

William A. Warriner, Tustin, Calif., assignor to Jackson & Perkins Company, Medford, Oreg.

Filed Apr. 30, 1975, Ser. No. 573,060

Int. Cl.[2] A01H 5/00

U.S. Cl. Plt.—29 1 Claim

This present invention relates to a new and distinct cultivar of rose plant of the floribunda class which was originated by me by crossing an unnamed cultivar with pollen of the cultivar Mary DeVor, U.S. Plant Pat. 2,838.

The primary objective of this breeding was to produce a new red flowered rose cultivar of the floribunda class particularly suitable for use as a greenhouse cut flower. This objective was substantially achieved as evidenced by the following unique combination of characteristics which are outstanding in the new cultivar and which distinguish it from its parents as well as from all other cultivars of which I am aware:

1. A vigorous, heavily branched, upright habit of growth.
2. Strong, long cutting stems.
3. Semi-glossy, large foliage, which generally has a longer, more pointed leaflet than its parent, Mary DeVor.
4. The shape of the receptacle is like a small apple, wide at the equator and constricted at the sepal juncture; the receptacle of Mary DeVor is widest at the point of attachment of the sepal.
5. The flower color from bud to open flower is similar to that of Mary DeVor, but the base of the petal is white and on Mary DeVor the base is yellow.
6. A petal count of 25–30 as compared to nearly 40 on Mary DeVor.

The cultivar differs from the cultivar Caliente, U.S. Plant Pat. 3,595, a red floribunda for greenhouse cut flower use, in several characteristics:

A. Larger, more pointed foliage
B. Darker bud color
C. More pointed bud form
D. Flower form is more regularly imbricated and generally larger.

Asexual reproduction of this new cultivar by budding, as performed at Wasco, Calif., proves that the foregoing characteristics and distinctions reproduce truly and are established and transmitted through succeeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose variety with color terminology in accordance with Wilson's Horticultural Color Chart, except where ordinary dictionary significance of color is indicated.

Parentage: Seedling.
*Seed parent.*—Unnamed cultivar.
*Pollen parent.*—Mary DeVor, U.S. Plant Pat. 2,838.
Classification:
*Botanical.*—Rosa hybrid.
*Commercial.*—Floribunda.

FLOWER

Observations made from specimens grown in a greenhouse at Irvine, Calif., January 1975.

Blooming habit: Recurrent, continuous.
Bud:
*Size.*—1" to 1¼" when petals start to unfurl.
*Form.*—Pointed ovoid.

*Color.*—When sepals first divide—slightly darker than Cardinal Red (822). When half blown; upper side of petals near Currant Red (821); lower side of petals near Currant Red (821/3). Lower surface is less glossy than upper surface.
*Sepals.*—Color: Outer surface Scheeles Green (860/3). Inner surface lighter than outer surface with only very little tomentum. Three appendaged sepals normally appendaged. Two unappendaged sepals hairy edged, plus a few stipitate glands.
*Receptacle.*—Color: Scheeles Green (860/3). Shape: Apple. Widest diameter at center of receptacle, not at top. Size: Relatively large. Surface: Smooth.
*Peduncle.*—Length: Very long. Surface: Glandular. Color: Scheeles Green (860%3). Strength: Mostly erect, slender.
*Opening.*—Slowly—with petal tips only slightly recurved.
Bloom:
*Size.*—Medium. Average size when fully expanded 2" to 2½".
*Borne.*—Singly or several together on strong canes.
*Stems.*—Long.
*Form.*—When first open, high centered.
*Petalage.*—Number of petals under normal conditions 25–30.
*Color.*—Center of flower: Upper side of petals near Currant Red (821). Reverse side of petals near Currant Red (821%3). Base of petals have very small area of yellow when young, fading to white in fully open flower. General tonality from a distance—Currant Red (821).
*Discoloration.*—General tonality at end of first day—Red (821). Third day—Currant Red (821).
Petals:
*Texture.*—Thin.
*Shape.*—Round.
*Form.*—Tips slightly recurved.
*Arrangement.*—Imbricated.
*Persistence.*—Drop off cleanly.
*Fragrance.*—Very slight.
*Lastingness.*—On the plant—very long. As cut flower—very long.
Reproductive parts:
*Stamens, anthers.*—Medium, many. Color—Amber Yellow (505). Arrangement—regular around styles.
*Filaments (threads).*—Color—Light Pink (Dictionary).
*Pollen.*—Amber Yellow (505/1).
*Styles.*—Color—Rose Red (724/1).
*Stigmas.*—Color—White.

PLANT

Form: Bush.
Growth: Very vigorous, upright, branching.
Foliage: Number of leaflets on normal mid-stem leaves, 5.
*Size.*—Large.
*Quantity.*—Normal.
*Color.*—New Foliage: Lighter than but near Garnet Brown (00918/3). Old Foliage: Near Spinach Green (0960). Semi-glossy.
*Shape.*—Oval pointed.
*Texture.*—Semi-glossy.
*Edge.*—Serrated.
*Serration.*—Single, small.
Petiole.—(*rachis*) — Color — Green. Underside—prickles.
*Stipules.*—Medium, smooth.
*Disease resistance.*—Fairly resistant to mildew under normal growing conditions at Irvine, Calif. Susceptible to mildew under severe conditions.

Wood:

*New wood.*—Color—Reddish. Bark—Smooth.

*Old wood.*—Color—Green. Bark—Smooth.

Prickles:

*Quantity.*—On main stalks from base—ordinary. On laterals from stalk—ordinary.

*Form.*—Narrow based, long, slightly hooked downwardly.

*Color when young.*—Red.

*Position.*—Irregular.

Small prickles:

*Quantity.*—On main stalks—none. On laterals—none.

I claim:

1. A new and distinct cultivar of rose plant of the floribunda class, substantially as herein shown and described, characterized particularly as to novelty by the unique combination of its vigorous growth, dark red, pointed buds, Currant Red open flowers, with a white base, apple shaped receptacle, and long oval pointed leaflets.

No references cited.

ROBERT E. BAGWILL, Primary Examiner

UNITED STATES PATENT OFFICE

CERTIFICATE OF CORRECTION

PATENT NO. : PP 3937

DATED : July 20, 1976

INVENTOR(S) : William A. Warriner

It is certified that error appears in the above-identified patent and that said Letters Patent are hereby corrected as shown below:

Column 2, line 15: "(860%3)" should be --(860/3)--.

Column 2, line 29: "(821%3)" should be --(821/3)--.

Column 2, line 34: Before "Red" insert --Currant--.

Signed and Sealed this

*Eighteenth* Day of *October 1977*

[SEAL]

*Attest:*

RUTH C. MASON
*Attesting Officer*

LUTRELLE F. PARKER
*Acting Commissioner of Patents and Trademarks*